United States Patent [19]

Miles

[11] 3,950,134

[45] Apr. 13, 1976

[54] ASSAY MACHINE AND METHOD

[75] Inventor: Laughton E. M. Miles, Stanford, Calif.

[73] Assignee: The Board of Trustees of the LeLand Stanford Junior University, Stanford, Calif.

[22] Filed: Sept. 20, 1974

[21] Appl. No.: 507,693

[52] U.S. Cl. ............ 23/230 B; 23/230 R; 23/230.3; 23/253 R; 23/259; 424/1.5; 424/12; 73/422 R

[51] Int. Cl.[2] .................. G01N 23/00; G01N 33/16

[58] Field of Search .......... 23/230 B, 230 R, 253 R, 23/230.3, 230.6; 424/12, 1.5

[56] References Cited

UNITED STATES PATENTS

| | | | |
|---|---|---|---|
| 3,681,030 | 8/1972 | Natelson | 23/253 R |
| 3,768,979 | 10/1973 | Mead | 23/253 R |
| 3,826,619 | 7/1974 | Bratu | 23/253 R |
| 3,832,138 | 8/1974 | Hirsch | 23/253 R |

*Primary Examiner*—Morris O. Wolk
*Assistant Examiner*—Sidney Marantz
*Attorney, Agent, or Firm*—Robert G. Slick

[57] ABSTRACT

An apparatus for conducting chemical assays features a coiled soft plastic tube as a reaction chamber. Along the length of the plastic tubing is a slit therein through which a needle-like member of a travelling dispenser injects samples to be analyzed. The injected samples may react with a reactant previously deposited in the interior of the plastic tube. The apparatus is applicable to carrying out radioimmunoassays.

6 Claims, 3 Drawing Figures

ASSAY MACHINE AND METHOD

The invention described herein was made in the course of work under a grant or award from the Department of Health, Education and Welfare.

SUMMARY OF THE INVENTION

Much work has been done on the identification of antibodies and antigens by the technique of immunoradiometric assay (IRMA) or by a further development of the technique known as 2-site IRMA.

In accordance with the former, an unknown antigen reacts with a soluble purified radioactive antibody. The radioactive complex which forms remains in solution and the excess unreacted radioactive antibody is removed by a second reaction with a solid phase antigen.

In accordance with the second or 2-site technique, an unknown antigen is insolubilized, as on the wall of a vessel, followed by reaction with an excess of a soluble labelled antibody. The labelled complex thus formed is insoluble and the excess unreacted labelled antibody can be washed away. The quantity of the radioactive complex formed is thus directly related to the quantity of the unknown antigen originally present. After the unreacted antibody is washed away, the quantity of the labelled complex can be determined using standard techniques (e.g. a gamma counter, recorder and integrator) for determining and recording radioactivity. The present invention relates primarily to a device and method of utilizing these IRMA techniques and the invention will be largely described in the terms of such techniques. However, as will become apparent later in the specification, the device and technique of the present invention have broad applicability and can be used in various other assays.

As was pointed out above, one of the preliminary steps in the normal 2-site assay is to first deposit an antigen in a vessel or some solid phase. In the past, this has been done in a test tube or the like and if a large number of assays are to be conducted or if it is desired to conduct an assay of a changing material such as running a continuous assay of the blood of a person, the number of tubes involved and the mechanical complications become almost insurmountable.

In accordance with the present invention, a device and method have been developed which permit a large number of assays to be run on a semi-continuous basis in a very small space.

Further, a test apparatus is provided which consists primarily of a resilient split plastic tubing which can be coiled, as is hereinafter described in detail, so that the apparatus for conducting a large number of tests occupies only a small space. The tubing is resilient and a needle can be inserted in the slit and moved along to deposit one or more of the reagents in a continuous manner throughout the length of the tubing as is hereinafter described in detail.

Normally, the tubing would first be coated with the antigen to be measured which would become insoluble and bind to the wall. A preferred method of insolubilizing the antigen is by reaction with a preliminary tube coating of specific antibodies. The antibodies are physically adsorbed onto the wall by filling the tube with the antibody solution diluted 1:1000 to 1:50,000 with a 0.02 M aqueous sodium bicarbonate solution having a pH of about 9.2. This could be done either by pouring the antibody solution through the tubing from one end to the other or by injecting the solution through the needle as it moves along the tubing through the slit. After this preliminary reaction, the solution is aspirated from one end of the tubing and the tubing rinsed with diluent. A series of samples of unknown antigen solutions are then introduced through the needle applicator as it moves along the tubing through the slit (Reaction 1). After Reaction 1, the tubing is evacuated by applying suction to the applicator as it again proceeds along the tubing. The radioactive antibody is then introduced into the tube (Reaction 2). This can be done either by repetition of the needle technique described above or the solution may be merely flowed through the tubing. The unreacted labelled material is then washed out of the tube, leaving the insolubilized complex of the labelled antibody and the unknown. The tubing is then read on a gamma counter to determine the amount of binding which has taken place with various samples throughout the length of the wall of the tube. Since there has been an excess of the labelled antibody, the amount of the unknown will be reflected in the amount of the complex formed at any given point on the tubing.

The tubing can be read by removing it from the apparatus and drawing it through a gamma counter or the gamma counter can be placed over the tubing and the tubing moved past the counter so that it is not necessary to remove the tubing from the holder.

Since the apparatus of the present invention is very compact, it lends itself well to techniques which require control of the environment during incubation or other periods. Thus, the device of the invention could easily be placed in a conventional refrigerator or oven to control the temperature at any or all stages of the process.

In general, the apparatus consists of a helical plastic tubing which can be rotated and wherein an auxiliary device is located adjacent the drum with means for moving the auxiliary device in synchronism with the movement of the tubing. The auxiliary device would normally carry a needle-like applicator which would fit within the slit of the tubing on the drum and which can be used to inject a reagent, diluent, or other material into the tubing. The auxiliary device can also be used to carry a knife to slit the tubing, i.e. in some applications of the device, the tubing can be placed on the drum or disc in an unslit condition and the auxiliary device will hold a knife to slit the tubing in a uniform manner. Similarly, the auxiliary device can carry a counter or other detection device for assaying the contents of the tube.

DESCRIPTION OF THE PREFERRED EMBODIMENTS

Preferably, the device of the present invention consists of a threaded drum which can be rotated on its axis with the auxiliary device positioned at one side of the drum. A driving means is provided for rotating the drum at a desired speed while a synchronized lead screw is connected to the auxiliary device so that the auxiliary device traverses with the lead of the threading on the drum and thus follows the tubing. The drum itself can be provided with an indexing groove thereon which causes the auxiliary device to traverse.

Normally, the drum is grooved so that the tubing will form a frictional fit in the grooves but the tubing can be fastened to the drum in other manners. By providing the frictional fit, the tubing can be readily replaced on the drum or stripped off the drum for assay.

A less preferred embodiment of the invention provides a tubing holder in the form of a disc with a spiral groove therein in the manner of a phonograph record. The auxiliary device is caused to traverse the radius of the disc to maintain a fixed relationship with the tubing.

The grooved tubing holder can be hollow and provided with internal inlets and outlets so that a cooling or heating fluid can be passed through the center of the tubing holder to maintain a desired temperature.

Preferably, when the needle technique is used to add a liquid reagent to the tubing, stiff needle extends for a short distance straight into the tube in a self-sealing relationship. Alternatively, the dispensing tube can be flexible and extend for several inches in a trailing relationship from the slit. In this manner, one can observe the delivery of material within the split tube and make any desired adjustments. Although a preferred material for the tubing is an olefin polymer such as polyethylene, any relatively soft, resilient plastic with self-sealing properties may be employed.

Figure 1:
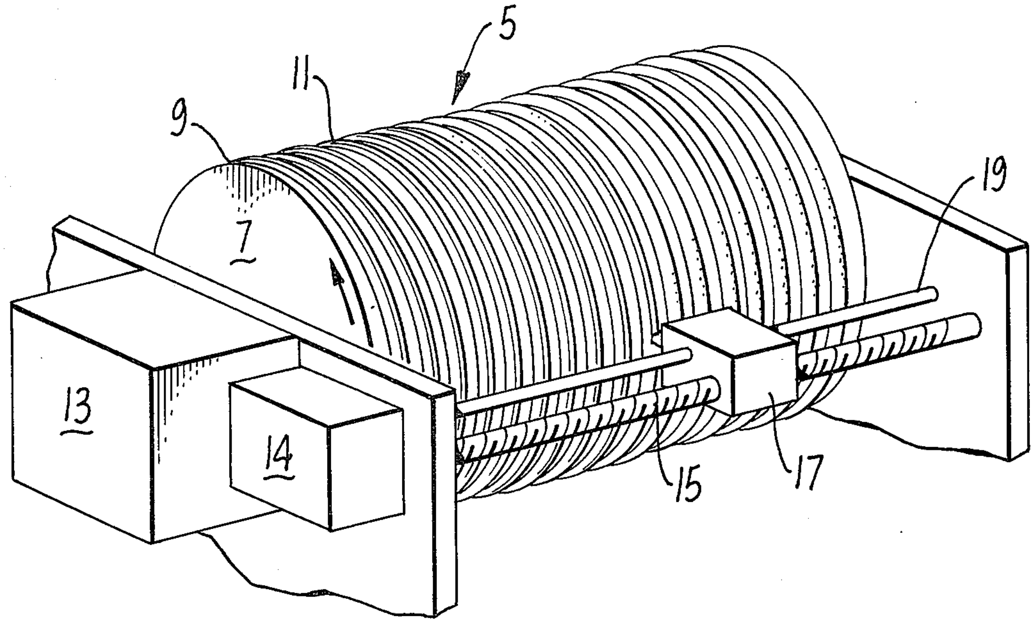
FIG. 1 is a perspective view of an assay device embodying the present invention.
Figure 2:
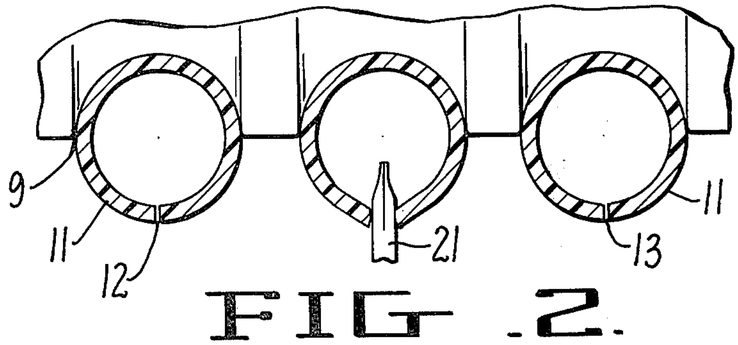
FIG. 2 is an enlarged section through a portion of the drum and tubing showing the method of injecting a liquid into the tubing.

Referring now to the drawings by reference characters there is shown in FIGS. 1 and 2 a drum generally designated 5 which consists of a cylinder 7 having a groove 9 or thread running the length thereof. A continuous length of plastic tubing 11 fits in groove 9 and the tubing has a continuous slit 12 running the length of the tubing. A motor 13 is provided for driving the cylinder at a desired speed. At one side of the cylinder 7 a lead screw is provided which is also driven by the motor 13 through gear box 14 in synchronism therewith. A needle holder 17 is slideably mounted on bar 19 and is driven by the lead screw 15. The lead of the threads on the cylinder and the screw and their respective speeds are selected to move the holder across the cylinder at the same rate as the groove 9 advances. Thus, as the drum 5 revolves, the needle holder 17 will move across the drum in synchronism with the threads on the drum.

The needle holder carries a hollow needle 21 which enters the slit 12 as is best seen in FIG. 2. It has been found that by proper selection of wall thickness and plastic, the tubing is self-sealing so that the needle can move through the tubing and deposit liquid therein, yet it will not permit any leakage to take place.

Figure 3:
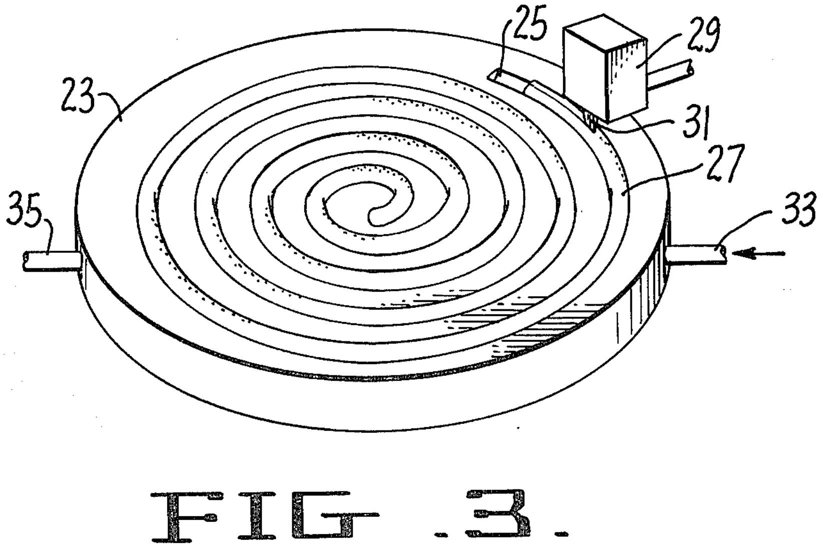
FIG. 3 is an alternate embodiment of the invention wherein the tubing is formed as a flat helix.

In FIG. 3 another embodiment of the invention is shown wherein a flat plate 23 is provided having a helical groove 25 therein. A slit tubing 27 lies in the groove while a needle holder 29 is supported above the tubing with needle 31 extending downwardly into the slit of the tubing as previously described. Means are provided, not illustrated, for rotating the plate 23 and for moving the holder 29 in and out so that it always stays above the groove as the tubing is rotated. If desired, the plate 23 can be made hollow with an inlet 33 and an outlet 35 for a heating or cooling fluid so that suitable conduits can be attached to the plate to flow a temperature controlling fluid through the plate and maintain it at a desired temperature. Similar conduits can be provided on drum 7.

In one practical embodiment of the device, the tubing consisted of 100 feet of heavy walled polyethylene tubing having an inside diameter of 1/16th of an inch. The motor rotated the cylinder at 5 revolutions per hour and the cylinder was about six inches in diameter and two feet long.

The following non-limiting example illustrates an assay conducted utilizing the device of the present invention:

EXAMPLE

Assay procedure using automated 2-site immunoradiometric (2-site IRMA) assay system The assay procedure was as follows. About 100 feet of polyethylene tubing is wound onto the drum and pressed down firmly into the spiral groove by a blunt plastic rod which moves mechanically along the drum in the place of the applicator.

Specific but unpurified antisera diluted 1:2000 with sodium bicarbonate 0.2 M pH 9.2, was pumped through the length of the tubing and left for 4 hours at room temperature. The tubing was then washed by an infusion of diluent solution (diluent = 0.05 M sodium barbitone, 0.1 M NaCl, 1% bovine serum albumin and 0.2% sodium azide). After the diluent was pumped out, the tubing was mechanically slit along its length, using a blade mounted on the applicator. Standard solutions of antigen in hormone-free human serum at a final dilution of 1:5 were picked up from a sampler using a variable speed pump, and pumped through the applicator and through the side of the assay tubing as the applicator "played" slowly down the length of the tubing. A dispensing tubing passed through the applicator and continued for 14 inches around the drum (inside the assay tubing) so that the delivery of antigen solution could be easily observed and the rates adjusted. Boluses of antigen solution were deposited into the interior of the tubing separated by air and by a wash with hormone-free serum diluted 1:5. The proximal end of the tubing was heat sealed. When all the standards and unknowns were inserted into the tubing, the applicator was removed and the distal end of the tubing heat sealed. After an incubation time of 24 hours the applicator was connected to suction and run again through the assay tubing in order to remove the sample.

A second reaction (using labelled antibody) was carried out in the same way, allowing a 48-hour reaction followed by a single wash with the diluent.

The tubing was slowly unwound from the drum through a manual gamma well counter, pulled by a small constant-speed electric motor. The radioactivity was recorded on a recorder and integrated using a rate-meter and integrator.

Although the above example shows a specific assay, it is obvious that the device of the present invention and the technique can be used for a variety of other assays. For instance, it is not necessary to utilize protein binding to the tube wall but the tube might first be filled with a solid phase non-specific adsorbent such as talc or charcoal and the liquid reagent added in one or more passes through the needle. Further, the invention is not limited to the use of radioactive agents but other detecting methods might be used, e.g. agents which fluorescence might be used and the degree of fluorescence detected rather than the radioactivity.

I claim:

1. An apparatus for conducting chemical assays comprising in combination:
a. a length of a flexible, soft plastic tubing,
b. a slit running the length of said tubing,
c. means for holding said tubing in a coiled configuration,
d. dispensing means including a needle-like member extending in self-sealing relationship into said slit, and
e. means for moving said dispensing means through the slit in said tubing.

2. The apparatus of claim 1 wherein the soft plastic tubing is wound on a threaded drum.

3. The apparatus of claim 1 wherein the soft plastic tubing is wound on a flat disc with a helical groove therein.

4. The apparatus of claim 2 having means for rotating said drum on its axis and having an auxiliary device mounted for movement adjacent to the drum parallel to its axis and means for traversing the auxiliary device in synchronism with the lead of the threaded drum.

5. The apparatus of claim 4 wherein said auxiliary device carries the dispensing means of paragraph (d).

6. A method of conducting an assay comprising the steps of:
a. providing an elongated continuous chamber,
b. depositing within said chamber throughout the length thereof a solid reactant,
c. injecting a liquid reactant in said chamber along the length of said chamber in a continuous manner, and
d. moving an analysis device along said chamber to analyze the results of the reaction between said solid and said liquid reactants.

* * * * *